(12) United States Patent
Wu

(10) Patent No.: US 8,475,422 B2
(45) Date of Patent: Jul. 2, 2013

(54) SPERM COLLECTOR WITH SQUEEZING FUNCTION

(75) Inventor: Wei Wu, Zhejiang (CN)

(73) Assignee: Lover Health Science and Technology Co., Ltd., Zhejiang (CN)

(*) Notice: Subject to any disclaimer, the term of this patent is extended or adjusted under 35 U.S.C. 154(b) by 79 days.

(21) Appl. No.: 13/165,828

(22) Filed: Jun. 22, 2011

(65) Prior Publication Data

US 2012/0215189 A1 Aug. 23, 2012

(30) Foreign Application Priority Data

Feb. 22, 2011 (CN) .................... 2011 2 0043933 U

(51) Int. Cl.
*A61F 5/41* (2006.01)

(52) U.S. Cl.
CPC .................................... *A61F 5/41* (2013.01)
USPC ............................................ 604/349; 600/38

(58) Field of Classification Search
USPC .............. 604/349, 317, 350–353; 600/38–39; 128/844, 917–918
See application file for complete search history.

(56) References Cited

U.S. PATENT DOCUMENTS

| | | | | |
|---|---|---|---|---|
| 1,585,861 A * | 5/1926 | Huff | ................................. | 600/39 |
| 2,433,538 A * | 12/1947 | Warner | ......................... | 604/353 |
| 2,686,519 A * | 8/1954 | Westerman | .................... | 604/347 |
| 2,699,781 A * | 1/1955 | Koch | ............................. | 604/352 |
| 2,705,951 A * | 4/1955 | Crowner | ........................ | 128/844 |
| 3,309,791 A * | 3/1967 | Kelley et al. | .................. | 434/225 |
| 3,401,696 A * | 9/1968 | O'Brien | ......................... | 604/347 |
| 3,602,923 A * | 9/1971 | Girala | ............................. | 4/144.1 |
| 3,648,700 A * | 3/1972 | Warner | ......................... | 128/844 |
| 3,781,922 A * | 1/1974 | Ericson | .......................... | 4/144.1 |
| 3,998,228 A * | 12/1976 | Poidomani | .................... | 604/351 |
| 4,074,712 A * | 2/1978 | Wright | ............................ | 600/39 |
| 4,232,675 A * | 11/1980 | Meldahl | ........................ | 604/353 |
| 4,312,350 A * | 1/1982 | Doan | ............................. | 604/349 |
| 4,407,275 A * | 10/1983 | Schroeder | ....................... | 600/38 |

(Continued)

FOREIGN PATENT DOCUMENTS

GB 2337001 A * 11/1999

OTHER PUBLICATIONS

English translation of Baidu Encyclopedia entry on Silastic fever tablets/an overview of the silicone rubber heat generation sheet, dated Apr. 1, 2013.*

*Primary Examiner* — Melanie Hand
*Assistant Examiner* — Paula Craig

(57) ABSTRACT

The present invention is a sperm collector with squeezing function. It includes a soft rubber body provided with a penis insertion passage and a container body provided with at least a top end cover and receives the soft rubber body. When the top end cover and the container body are engaged, the soft rubber body is confined within a cavity formed by the top end cover and the container body. When the top end cover is disengaged, a front end portion of the soft rubber body protrudes out of an opening of the container body. A pressing means is provided at a middle lower portion of the container body. When using the present invention, the user could press the pressing means to squeeze the penis insertion passage of the sperm collector. Accordingly, stimulation to penis is increased and better effect of sperm collection is achieved. In particular, since the present invention is also provided with a heating rod, lubricant pockets and electrical vibrators, which enable the user to reach a climax as quick as possible, thereby further enhancing the effect of sperm collection.

6 Claims, 4 Drawing Sheets

U.S. PATENT DOCUMENTS

| | | | | |
|---|---|---|---|---|
| 4,429,689 A * | 2/1984 | Yanong | | 600/39 |
| 4,468,557 A * | 8/1984 | Bylin et al. | | 219/535 |
| 4,580,553 A * | 4/1986 | Laib | | 601/102 |
| 4,620,531 A | 11/1986 | Dyer | | 604/349 |
| 4,655,755 A * | 4/1987 | Ruffini | | 604/352 |
| 4,707,864 A * | 11/1987 | Ikematsu et al. | | 4/144.3 |
| 4,744,352 A * | 5/1988 | Emery | | 604/349 |
| 4,846,197 A * | 7/1989 | Benjamin | | 128/844 |
| 4,872,463 A * | 10/1989 | Nishizono | | 128/844 |
| 4,881,553 A * | 11/1989 | Grossman | | 128/844 |
| 4,895,140 A * | 1/1990 | Bellak | | 600/39 |
| 4,899,737 A * | 2/1990 | Lazarian | | 602/22 |
| 4,919,149 A * | 4/1990 | Stang | | 128/842 |
| 5,024,852 A * | 6/1991 | Busnel et al. | | 427/2.3 |
| 5,103,810 A * | 4/1992 | Chang | | 600/39 |
| D330,762 S * | 11/1992 | Anderson et al. | | D24/108 |
| 5,191,902 A * | 3/1993 | Wilk | | 128/844 |
| 5,360,390 A | 11/1994 | Maanum | | 600/39 |
| 5,370,131 A * | 12/1994 | Hess | | 128/844 |
| 5,377,692 A * | 1/1995 | Pfeil | | 128/844 |
| 5,437,652 A * | 8/1995 | Anatolievich | | 604/349 |
| 5,454,379 A * | 10/1995 | Shepherd | | 128/842 |
| 5,458,559 A * | 10/1995 | Gauntlett | | 600/38 |
| 5,466,235 A * | 11/1995 | Shubin, Sr. | | 600/38 |
| 5,501,650 A * | 3/1996 | Gellert | | 600/38 |
| 5,540,670 A * | 7/1996 | Lindholm-Ventola | | 604/349 |
| 5,626,149 A * | 5/1997 | Schwartz | | 128/842 |
| 5,640,973 A * | 6/1997 | Blinn | | 128/844 |
| 5,669,869 A * | 9/1997 | Strom | | 600/38 |
| 5,685,871 A * | 11/1997 | Lindholm-Ventola | | 604/349 |
| 5,695,446 A * | 12/1997 | Lindholm-Ventola | | 600/38 |
| 5,769,090 A * | 6/1998 | Brown | | 128/883 |
| 5,782,818 A * | 7/1998 | Shubin | | 604/349 |
| 5,885,205 A * | 3/1999 | Kassman | | 600/38 |
| 5,885,233 A * | 3/1999 | Adachi | | 601/138 |
| 5,954,054 A * | 9/1999 | Johnson | | 128/844 |
| 6,090,088 A * | 7/2000 | Nichols | | 604/347 |
| 6,113,532 A * | 9/2000 | Yap | | 600/38 |
| 6,117,120 A * | 9/2000 | Heininger | | 604/349 |
| 6,149,580 A * | 11/2000 | Dabney | | 600/38 |
| 6,419,665 B1 * | 7/2002 | Cohen | | 604/349 |
| 6,436,031 B1 * | 8/2002 | Salib | | 600/39 |
| 6,531,771 B1 * | 3/2003 | Schoenstein et al. | | 257/720 |
| 6,599,236 B1 * | 7/2003 | Castro | | 600/38 |
| 6,651,668 B1 * | 11/2003 | Praml | | 128/844 |
| 7,217,239 B1 * | 5/2007 | Dyer | | 600/33 |
| 8,052,730 B2 * | 11/2011 | Brown et al. | | 607/108 |
| 2002/0032419 A1 * | 3/2002 | Barth | | 604/349 |
| 2004/0039248 A1 * | 2/2004 | Vayer | | 600/38 |
| 2005/0081864 A1 * | 4/2005 | Carnevale | | 128/844 |
| 2005/0283127 A1 * | 12/2005 | Miskie | | 604/349 |
| 2006/0264856 A1 * | 11/2006 | Wong | | 604/349 |
| 2007/0186935 A1 * | 8/2007 | Wang et al. | | 128/844 |
| 2007/0261700 A1 * | 11/2007 | Chan | | 128/844 |
| 2008/0004577 A1 * | 1/2008 | Matsuura | | 604/317 |
| 2008/0065033 A1 * | 3/2008 | Matsuura | | 604/349 |
| 2008/0082028 A1 * | 4/2008 | Blevins | | 601/72 |
| 2008/0230073 A1 * | 9/2008 | Nan | | 128/844 |
| 2008/0294130 A1 * | 11/2008 | Simmet | | 604/349 |
| 2009/0137974 A1 * | 5/2009 | Yvoz | | 604/349 |
| 2010/0126513 A1 * | 5/2010 | Hui | | 128/844 |
| 2011/0009691 A1 * | 1/2011 | Stevens | | 600/38 |

* cited by examiner

SPERM COLLECTOR WITH SQUEEZING FUNCTION

This application claims priority to Chinese Patent Application No. 201120043933.0 filed Feb. 22, 2011.

BACKGROUND OF THE INVENTION

The present invention relates to a sperm collector and more specifically relates to a sperm collector with squeezing function.

Currently existing sperm collector mainly comprises a soft rubber body provided with a penis insertion passage and a container body provided with at least an end cover to receive the soft rubber body. When the end cover is closed, the soft rubber body is confined within a cavity formed by the end cover and the container body. When the end cover is opened, a front end portion of the soft rubber body protrudes out of the container body's opening so that a user of the sperm collector could grab the container body and uses the sperm collector directly. Sperm collector in such a structure has the following disadvantages: Firstly, as the container body has a certain degree of hardness (to support the soft rubber body), the user is not able to press against an outer wall of the container body to squeeze the penis insertion passage of the soft rubber body received therein and therefore the stimulation effect on penis is not sufficient; Secondly, due to the lack of heating function, it may cause discomfort to the penis when the sperm collector is used in an environment under relatively low temperature (for example winter) and sperm collection effect is therefore affected; Thirdly, due to the lack of vibration function, the user is not easy to reach a climax when using the sperm collector.

BRIEF SUMMARY OF THE INVENTION

The object of the present invention is to provide a sperm collector with squeezing function. By pressing against the sperm collector, the penis insertion passage of the sperm collector could be squeezed so as to increase stimulation to penis and achieve better effect of sperm collection.

To attain this, the present invention could adopt the following technical proposal:

A sperm collector with squeezing function according to the present invention comprises a soft rubber body provided with a penis insertion passage and a container body provided with at least a top end cover and receives the soft rubber body. When the top end cover and the container body are engaged, the soft rubber body is confined within a cavity formed by the top end cover and the container body. When the top end cover is disengaged, a front end portion of the soft rubber body protrudes out of an opening of the container body. A pressing means is provided at a middle lower portion of the container body.

The pressing means comprises a soft rubber handle sleeve. The soft rubber handle sleeve surrounds an outer wall of the container body. Through holes are arranged on the container body under the soft rubber handle sleeve.

A heating rod is provided in a middle portion of an inner wall of an end wall of the top end cover. When the top end cover and the container body are engaged, the heating rod is inserted inside the penis insertion passage. When the top end cover is disengaged, the heating rod is removed from the penis insertion passage.

The heating rod comprises a hollow rod body with an outer diameter ranging from 16 to 38 mm and a length ranging from 80 to 250 mm. The hollow rod body is disposed therein with an electrical heating component and a temperature controller for controlling the electrical heating component. The electrical heating component and the temperature controller are electrically connected with a power supply in voltage ranging from 2 to 24V via wires, wire contacts and a switch disposed on the container body.

The electrical heating component comprises a tubular rubber member, and a silicon rubber heating chip wrapping around an outer surface of the rubber member. The temperature controller comprises a temperature sensor and a circuit board. A bottom end cover is provided at another end of the container body. The power supply in voltage ranging from 2 to 24V is in form of batteries disposed at the bottom end cover. The bottom end cover is disposed with charging plugholes or charging contacts for external connection with a charger and a soft rubber stopper for blocking the charging plugholes.

The hollow rod body has an outer diameter ranging from 16 to 38 mm and a length ranging from 80 to 250 mm.

The container body is formed by connecting a large cylindrical body and a small cylindrical body both with circular cross sections. The soft rubber handle sleeve surrounds an outer wall of the small cylindrical body. The through holes are two rectangular through holes symmetrically arranged on two sides of the small cylindrical body. Each of the two rectangular through holes ranges from 30 to 150 mm long and from 20 to 65 mm wide. Electrical vibrators are provided at least on one side of the soft rubber body. The electrical vibrators are electrically connected with the batteries disposed at the bottom end cover via wires, wire contacts and the switch disposed on the container body.

In a condition under which the soft rubber body is received inside the container body, a locking ring is provided in a locking groove disposed at an upper portion of an inner wall of the large cylindrical body and an annular groove disposed on the soft rubber body at a position corresponding to the locking groove.

Lubricant pockets are provided on the soft rubber body at positions corresponding to the rectangular through holes. Each of the lubricant pockets is provided with an oil hole facing towards the penis insertion passage. The oil hole is open upon a condition of being squeezed.

An advantage of the present invention is that: Since the pressing means is provided at a middle lower portion of the container body, the user could squeeze the penis insertion passage of the sperm collector by pressing the pressing means. Accordingly, stimulation to penis is increased and better effect of sperm collection is achieved, as compared with the sperm collectors according to the prior arts.

Another advantage of the present invention is that: The heating rod is provided in the middle of an inner wall of an end wall of the top end cover; the heating rod is inserted inside the penis insertion passage when the top end cover and the container body are engaged and the heating rod is removed from the penis insertion passage when the top end cover is disengaged. Structure of this kind could enable fast and convenient insertion of the heating rod inside the penis insertion passage of the sperm collector to heat up the sperm collector upon engagement of the top end cover, so as to overcome the disadvantage of causing discomfort to penis when currently existing sperm collector is used in an environment under relatively low temperature. Better effect of sperm collection could therefore be achieved. Also, structure of this kind is suitable for sperm collector in any shape.

A further advantage of the present invention is that: By supplying power in low voltage, the present invention has a high heating efficiency and is safe and reliable. By means of the silicon rubber heating chip and the temperature controller, the present invention achieves evenly distributed heating effect and precise temperature control. Provision of the electrical vibrators could enable user to reach a climax as quick as possible. The provision of the locking ring provides a fixing function so as to ensure that the soft rubber body would not easily fall out of the container body after it is received in the container body; besides, it is also convenient to remove the soft rubber body for cleaning. Also, the lubricant pockets are provided on the soft rubber body at positions corresponding to the rectangular through holes and oil holes facing towards the penis insertion passage are provided on the lubricant pockets, and according to this kind of structure, when the pressing means is pressed, the lubricant pockets are squeezed and under such a condition of being squeezed, the oil holes are forced to open under pressure and the lubricant inside the lubricant pockets is then ejected inside the penis insertion passage to lubricate the penis insertion passage to further enhance the effect of sperm collection.

DETAILED DESCRIPTION OF THE INVENTION

Figure 1:
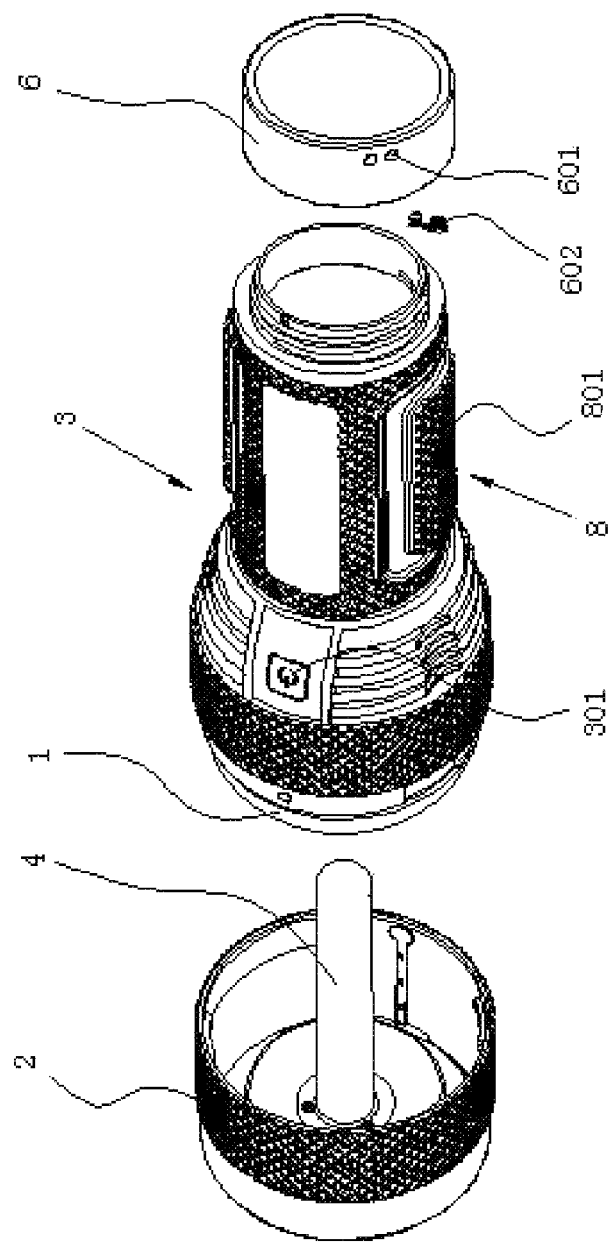
FIG. 1 is a three dimensional illustration of a structure of the present invention in an exploded view.
Figure 2:
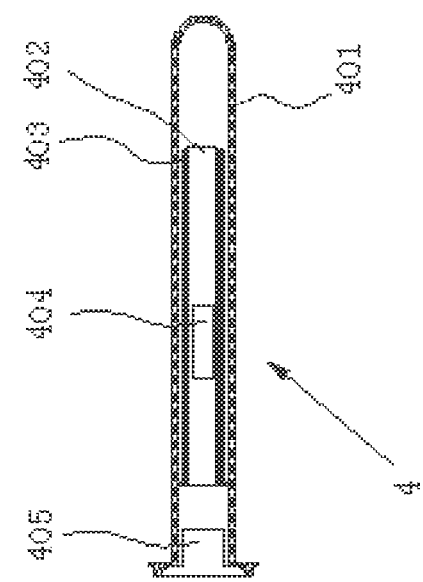
FIG. 2 is an illustration of a structure of the heating rod as shown in FIG. 1.
Figure 3:
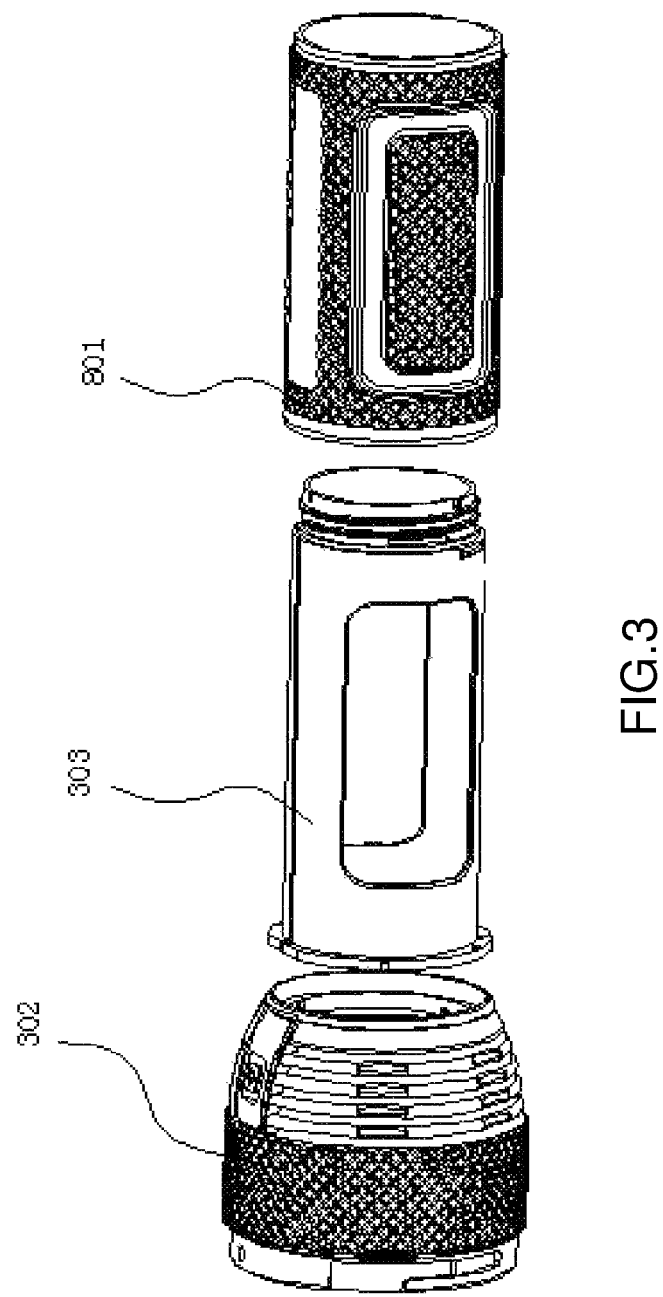
FIG. 3 is a three dimensional illustration of a structure of the container body and that of the pressing means as shown in FIG. 1 in an exploded view.
Figure 4:
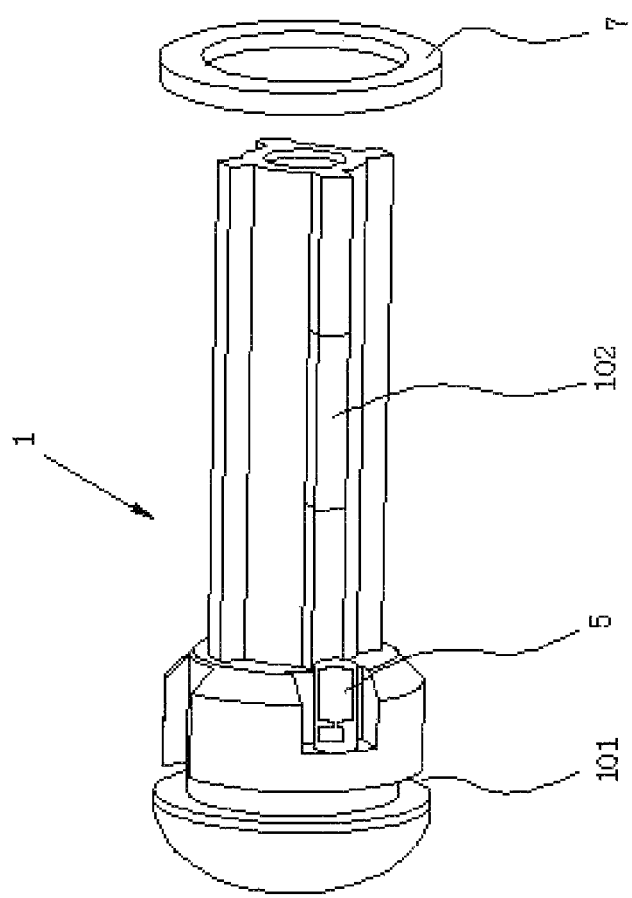
FIG. 4 is a three dimensional illustration of a structure of the soft rubber body as shown in FIG. 1.

As shown in FIG. 1 to FIG. 4, a sperm collector with squeezing function according to the present invention comprises a soft rubber body 1 provided with a penis insertion passage, and a container body 3 which receives the soft rubber body 1. The container body 3 is disposed with a top end cover 2 at an upper end thereof, and a bottom end cover 6 at a bottom end thereof. When the top end cover 2, the bottom end cover 6 and the container body 3 are engaged, the soft rubber body 2 is confined within a cavity formed by the top end cover 2, the bottom end cover 6 and the container body 3. When the top end cover 2 is disengaged, a front end portion of the soft rubber body 2 protrudes out of an opening at the upper end of the container body 3. A pressing means 8 is provided at a middle lower portion of the container body 3. The container body 3 is preferably formed by connecting a large cylindrical body 302 and a small cylindrical body 303 both with circular cross sections; more specifically, the large cylindrical body 302 is gradually reduced in diameter towards its connection end opening and the connection end opening is engaged with the small cylindrical body 303 by snap connection, screw connection or glue. The pressing means 8 comprises a soft rubber handle sleeve 801. The soft rubber handle sleeve 801 surrounds an outer wall of the small cylindrical body 303. On two sides of the small cylindrical body 303 under the soft rubber handle sleeve 801, two rectangular through holes are arranged symmetrically. Each of the two rectangular through holes ranges from 30 to 150 mm long (preferably 100 mm long) and from 20 to 65 mm wide (preferably 50 mm wide). When the user presses the soft rubber handle sleeve 801 by hand, pressure is transmitted to the soft rubber body 1 via the rectangular through holes and thereby squeezing the penis insertion passage of the sperm collector. Accordingly, stimulation to penis is increased and better effect of sperm collection is achieved, as compared with the sperm collectors according to the prior arts.

Two electrical vibrators 5 are provided symmetrically on two sides of the soft rubber body 1. The electrical vibrators 5 are electrically connected with batteries disposed at the bottom end cover 6 via wires, wire contacts disposed between the top end cover 2 and the large cylindrical body 302, wire contacts disposed between the bottom end cover 6 and the small cylindrical body 303 and a switch 301 disposed on the container body 3.

A heating rod 4 could also be provided in a middle portion of an inner wall of an end wall of the top end cover 2. When the top end cover 2 and the container body 3 are engaged, the heating rod 4 is inserted inside the penis insertion passage. When the top end cover 2 is disengaged, the heating rod 4 is removed from the penis insertion passage. The heating rod 4 comprises a hollow rod body 401 with an outer diameter ranging from 16 to 38 mm (preferably 24 mm) and a length ranging from 80 to 250 mm (preferably 160 mm). The hollow rod body 401 is disposed therein with an electrical heating component and a temperature controller for controlling the electrical heating component. The electrical heating component comprises a tubular rubber member 402, and a silicon rubber heating chip 403 wrapping around an outer surface of the rubber member 402. The temperature controller comprises a temperature sensor 404 and a circuit board 405. The electrical heating component and the temperature controller are electrically connected with the batteries disposed at the bottom end cover 6 via wires, wire contacts and the switch 301 disposed on the container body 3. The bottom end cover 6 is disposed with charging plugholes 601 or charging contacts for external connection with a charger and a soft rubber stopper 602 for blocking the charging plugholes 601. External power sources could recharge the batteries via the charging plugholes 601 or the charging contacts.

In a condition under which the soft rubber body 1 is received inside the container body 3, a locking ring 7 is provided in a locking groove disposed at an upper portion of an inner wall of the large cylindrical body 302 and an annular groove 101 disposed on the soft rubber body 1 at a position corresponding to the locking groove.

Lubricant pockets 102 are provided on the soft rubber body 1 at positions corresponding to the rectangular through holes. Each of the lubricant pockets 102 is provided with an oil hole facing towards the penis insertion passage. In a condition when the oil hole is not under pressure, the oil hole is closed by the elasticity of its own rubber body. When the pressing means is pressed, the lubricant pockets are squeezed and under such a condition of being squeezed, the oil hole is forced to open under pressure and the lubricant inside the lubricant pocket is then ejected inside the penis insertion passage to lubricate the penis insertion passage to further enhance the effect of sperm collection.

What is claimed is:

1. A sperm collector with squeezing function comprising:
   a soft rubber body (1) having a penis insertion passage;
   a container body (3) having through holes and containing the soft rubber body (1);
   a top end cover (2) capable of being engaged with the container body (3);
   a pressing unit (8), when the sperm collector is disposed vertically with the top end cover (2) towards the sky and the container body towards the earth, the pressing unit (8) disposed at a middle lower portion of the container body (3), the pressing unit (8) including a soft rubber handle sleeve (801), the soft rubber handle sleeve (801)

surrounding an outer wall of the container body (3) the through holes disposed on the container body (3) under the soft rubber handle sleeve (801); and a heating rod (4) disposed in a middle portion of an inner wall of the top end cover (2), wherein when the top end cover (2) and the container body (3) are engaged, the soft rubber body (1) is confined within a cavity formed by the top end cover (2) and the container body (3), and the heating rod (4) is inserted inside the penis insertion passage; and when the top end cover (2) is disengaged, a front end portion of the soft rubber body (1) protrudes out of an opening of the container body (3), and the heating rod (4) is removed from the penis insertion passage.

2. The sperm collector with squeezing function as in claim 1, wherein the heating rod (4) comprises a hollow rod body (401) with an outer diameter ranging from 16 to 38 mm and a length ranging from 80 to 250 mm, an electrical heating component and a temperature controller for controlling the electrical heating component are disposed in the hollow rod body (401); and the sperm collector further includes a switch (301) disposed on the container body (3), the electrical heating component and the temperature controller are electrically connected with a power supply in voltage ranging from 2 to 24V via wires, wire contacts and the switch (301).

3. The sperm collector with squeezing function as in claim 2, wherein the electrical heating component comprises a tubular rubber member (402), and a silicon rubber heating chip (403) wrapping around an outer surface of the rubber member (402); and the temperature controller comprises a temperature sensor (404) and a circuit board (405); and the sperm collector further includes a bottom end cover (6) disposed at another end of the container body (3); and the power supply in voltage ranging from 2 to 24V is in form of batteries disposed at the bottom end cover (6); and the bottom end cover (6) is disposed with charging plugholes (601) or charging contacts for external connection with a charger, the bottom end cover (6) includes a soft rubber stopper (602) for blocking the charging plugholes (601).

4. The sperm collector with squeezing function as in claim 3, wherein the container body (3) includes a large cylindrical body (302) and a small cylindrical body (303) both with circular cross sections; and the soft rubber handle sleeve (801) surrounds an outer wall of the small cylindrical body (303); and the through holes are two rectangular through holes symmetrically arranged on two sides of the small cylindrical body (303); and each of the two rectangular through holes ranges from 30 to 120 mm long and from 20 to 65 mm wide; and the sperm collector further includes electrical vibrators (5) disposed at least on one side of the soft rubber body (1); and the electrical vibrators (5) are electrically connected with the batteries disposed at the bottom end cover (6) via wires, wire contacts and the switch (301) disposed on the container body (3).

5. The sperm collector with squeezing function as in claim 4, wherein in a condition under which the soft rubber body (1) is received inside the container body (3), a locking ring (7) is provided in a locking groove disposed at an upper portion of an inner wall of the large cylindrical body (302) and an annular groove (101) disposed on the soft rubber body (1) at a position corresponding to the locking groove.

6. The sperm collector with squeezing function as in claim 5, wherein lubricant pockets (102) are provided on the soft rubber body (1) at positions corresponding to the rectangular through holes; and each of the lubricant pockets (102) is provided with an oil hole facing towards the penis insertion passage; and the oil hole is open upon a condition of being squeezed.

\* \* \* \* \*